US 6,630,180 B1

(12) United States Patent
Klein et al.

(10) Patent No.: US 6,630,180 B1
(45) Date of Patent: Oct. 7, 2003

(54) DIMETHICONE COPOLYOL RASPBERRIATE AS A DELIVERY SYSTEM FOR NATURAL ANTIOXIDANTS

(75) Inventors: Kenneth Klein, Fair Lawn, NJ (US); Irwin Paleksky, Clifton, NJ (US); Anthony J. O'Lenick, Jr., Dacula, GA (US)

(73) Assignee: Zenitech LLC, Old Greenwich, CT (US)

( * ) Notice: Subject to any disclaimer, the term of this patent is extended or adjusted under 35 U.S.C. 154(b) by 0 days.

(21) Appl. No.: 10/291,570

(22) Filed: Nov. 12, 2002

(51) Int. Cl.$^7$ ................................. A61K 35/78
(52) U.S. Cl. .................................... 424/765
(58) Field of Search ............................ 424/765; 554/77

(56) References Cited

U.S. PATENT DOCUMENTS

| 4,724,248 A | 2/1988 | Dexter et al. |
| 6,391,345 B1 * | 5/2002 | Heeg et al. |

OTHER PUBLICATIONS

Wohlman, Alan. Cosmetics & Tolietries (1997), vol. 112: 83–87. A meadowfoam seed oil derivative and its activity on human hair.*

Cseh, Jozsef. Elelmezes Ipar (1984), vol. 38: 375–378. Studies on the dithiocarbamate trace content of fruit juices produced by diffusion and heat treatment. Abstract only.*

Dahms, Gerd H et al. Cosmetics & Tolietries (1995), vol. 110: 91–100. New formulation possibilities offered by silicone copolyols.*

* cited by examiner

*Primary Examiner*—Christopher R. Tate
*Assistant Examiner*—Michele C. Flood

(57) ABSTRACT

The invention relates to raspberry seed oil derivatives prepared by the reaction of dimethicone copolyol and cold pressed raspberry seed oil. The choice of cold pressed raspberry seed oil as a raw material in the preparation of the compounds is critical, since it has been found that the cold pressed raspberry seed oil contains antioxidants, antimicrobial compounds and which when reacted with a water soluble or water dispersible silicone result in products that deliver said actives to the skin and hair, resulting in protection of the skin and hair from environmental factors such as acid rain, ozone attack and UV degradation.

20 Claims, No Drawings

DIMETHICONE COPOLYOL RASPBERRIATE AS A DELIVERY SYSTEM FOR NATURAL ANTIOXIDANTS

BACKGROUND OF THE INVENTION

The present invention relates to raspberry seed oil derivatives derived by the reaction of dimethicone copolyol and cold pressed raspberry seed oil. The choice of cold pressed raspberry seed oil as a raw material in the preparation of the compounds of the present invention is critical, since it has been found that the cold pressed raspberry seed oil contains a unique antioxidant which when reacted with a water soluble or water dispersible silicone result in products that deliver said actives to the skin and hair, resulting in protection of the skin and hair from environmental factors such as acid rain, ozone attack and UV degradation.

U.S. Pat. No. 6,391,345 issued May 2002 describes the refining of cold pressed raspberry seed oil, and is incorporated herein by reference. American cranberries, Vaccinium macrocarpon, are native plants of open, acid peat bogs in North America. Raspberry plants are evergreen perennial vines that produce runners and upright branches with terminal flower buds.

Raspberries have historically been harvested and either ingested as whole berries, such as in raspberry sauce, or have been processed for their juice. Pulp remaining after raspberry juice extraction processing has historically been regarded as an undesirable waste product with little or no utility.

Raspberries are grown all over the world. They are a popular food, consumed in large quantities.

Raspberries contain ellagic acid ($C_{14}H_6O_8$). This acid is a non-flavonoid polyphenol present in the form of hydrolysable tannins, which has been found to protect chromosomes from radiation induced lipid peroxidation. chromosomes from radiation induced lipid peroxidation. the bitter taste.

Raspberry oil contains a high level of omega 3 and omega 6 linoleic acid. These are essential fatty acids. Under normal circumstances, oils useful in the cosmetic industry are refined with a variety of steps that are designed to maximize triglyceride content, and minimize color and odor. These steps include steam distillation, a process in which steam is sparged through the oil to remove odor and color bodies and solvent extraction with compounds like hexane, which remove additional odor and color bodies. We have learned that these processes, while improving color and odor, remove many of the desirable "active" materials. What results is a light color, low odor triglyceride with no appreciable added skin benefits. We have surprisingly learned that when the raspberry seed oil that is cold processed is reacted with specific water-soluble silicone compounds, the actives (normally removed in non-cold press process) remain in the product, become water-soluble and have outstanding activity on the skin. In essence two things happen when the cold pressed raspberry seed oil is reacted with dimethicone copolyol. First the triglyceride reacts with the hydroxyl group of the silicone compound, giving a water-soluble ester. Secondly, the water-soluble ester solubilized the active components there as a consequence of cold pressing. Thirdly, these very desirable materials are deposited on the skin by the silicone fatty ester, based upon its proclivity to remain on the skin. The result is a unique delivery of the actives to the skin from totally natural fruit oil.

Silicone esters are known materials. U.S. Pat. No. 4,724,248 issued February 1988 to Dexter et al is the first patent to disclose silicone fatty esters. O'Lenick et al in U.S. Pat. No. 5,136,063 issued Aug. 4, 1992 later expanded the field. However these patents did not disclose or suggest the possibility of using cold pressed raspberry seed oil that is rich in antioxidants and other actives that could be delivered to the skin using a specific silicone ester as a delivery molecule.

SUMMARY OF THE INVENTION

The present invention relates to a series of silicone compounds derived from the reaction of cold pressed raspberry oil and specific silicone compounds.

The present invention also relates to a process of treating hair and skin which comprises contacting the hair and skin with an effective anti-oxidant containing amount of a raspberry silicone compound of the preset invention. de

DETAILED DESCRIPTION OF THE INVENTION

U.S. Pat. No. 6,391,345 issued May 2002 describes a cold pressed process for cranberry oil. We have surprisingly found that if the same process is used on raspberry oil specific antioxidant materials that are removed by more aggressive refining processes like solvent extraction. These compounds surprisingly survive the reaction with dimethicone copolyol and result in a water-soluble delivery system for these very desirable natural compounds.

Also critical to the practice of the present invention is the fatty composition of the cold pressed raspberry oil. This raspberry oil has a substantially clear appearance with a pale yellow color.

Cold Pressed Raspberry Oil is a triglyceride conforming to the following structure:

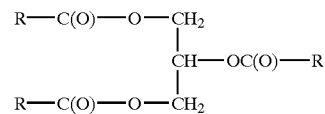

The oil is referred to as Rubus idaeus seed oil and has a CAS number of 381718-28-1

The R—C(O)— group has the following composition:

| Component | % Weight |
| --- | --- |
| 18:1 oleic | 10–20 |
| 18:2 linoleic | 30–40 |
| 18:3 linolenic (alpha) | 45–55 |
| alpha tocopherol | 46 mg/gram |
| Ellagic Acid | 450–650 ppm |

Distribution by type of fatty group

| Component | % Weight |
| --- | --- |
| Saturated | 3% |
| Polyunsaturated content | 86% |
| Mono unsaturated | 11% |

The oil contains the following very critical "active" components for skin and hair care:

| Material | Concentration |
| --- | --- |
| 18:3 linolenic (alpha) | 45–55% |
| alpha tocopherol | 46 mg/gram |
| Ellagic Acid | 450–650 ppm |

As can be seen, the cold pressed raspberry seed oil is a rich source of compounds having important properties when applied to hair and skin. The cold pressed raspberry oil can shield against UV-A induced damage by scattering light as well as by light spectrum absorption. The cold pressed raspberry oil has, then activity as a broad spectrum UV protectant. The raspberry oil may be used alone or in combination with other conventional sunscreens.

The ability to make derivatives of the oil in which the protection of the components of the cold pressed oil remain functional is a major aspect of the present invention.

Cold pressed raspberry seed oil has a very high concentration of gamma tocopherol. This level is much higher than is found in oils such as safflower and grape, which are 11 and 33, respectively. The gamma tocopherol has the most antioxidant capacity of all of the tocopherols and contributes to the stability of highly unsaturated oils in the raspberry oil. It is believed that the presence of the high gamma tocopherol concentration makes raspberry oil an excellent additive to animal food-both human and non-human. The gamma tocopherol may be as important as alpha tocopherol in preventing degenerative diseases.

Cold pressed raspberry seed oil has a high linolenic acid content. Linolenic acid has been implicated as a food additive and nutraceutical in preventing coronary heart disease and cancer. Raspberry oil also has a high polyunsaturated: saturated ratio in a neutral lipid fraction, of 10:1. This ratio is regarded as having value in reducing serum cholesterol, atherosclerosis and in preventing heart disease.

Cold pressed raspberry seed oil has a rather dark yellow to orange color because it contains carotenoids. The carotenoids are usable as colorant substitutes for materials such as carotenes, annotos, and apocarotenals used in the nutraceutical and oil industries.

The cold pressed raspberry seed oil, containing all of the above desirable compounds, is reacted with a dimethicone copolyol conforming to the following structure:

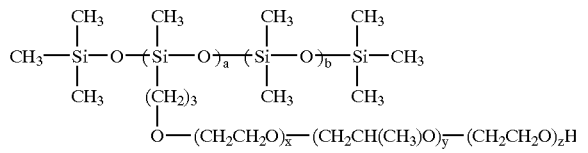

wherein a is an integer ranging from 1 to 20;

b is an integer ranging from 0 to 200;

x, y and z are independently integers ranging from 0 to 20, with the proviso that x+y+z is equal to or greater than 5.

To provide an ester conforming to the following structure:

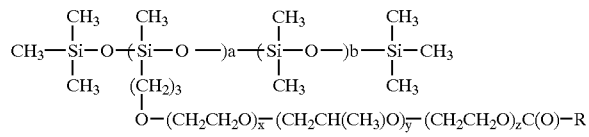

wherein a is an integer ranging from 1 to 20;

b is an integer ranging from 0 to 200;

x,y and z are independently integers ranging from 0 to 20, with the proviso that x+y+z is greater than 5.

R is derived from cold pressed raspberry seed oil and has the composition;

| Component | % weight |
| --- | --- |
| 18:1 oleic | 10–20 |
| 18:2 linoleic | 30–40 |
| 18:3 linolenic (alpha) | 45–55 |
| alpha tocopherol | 46 mg/gram |
| Ellagic Acid | 450–650 ppm |

The current invention describes a composition, which is prepared by the reaction esterification reaction of:

(1) cold pressed raspberry seed oil (2) a dimethicone copolyol conforming to the following structure

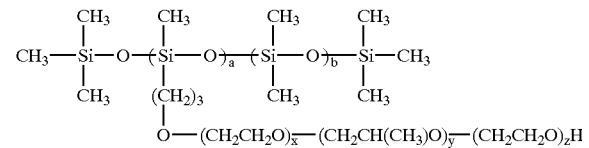

wherein a is an integer ranging from 1 to 20;

b is an integer ranging from 0 to 200;

x,y and z are independently integers ranging from 0 to 20, with the proviso that x+y+z is greater than 5.

The compounds of the present invention deliver these active products to skin. and the presence of the silicone surfactant allows the active to be efficiently deposited on the skin.

PREFERRED EMBODIMENT

In a preferred embodiment said esterification is conducted at temperature of between 180 and 220 C.

In a preferred embodiment said esterification reaction is conducted using a tin catalyst.

In a preferred embodiment a is 4, b is 0, x is 0, y is 0 and z is 5.

In a preferred embodiment a is 4, b is 8, x is 5, y is 4, and z is 5.

In a preferred embodiment a is 4, b is 10, x is 20, y is 20, and z is 20.

In a preferred embodiment a is 4, b is 100, x is 20, y is 0, and z is 20.

In a preferred embodiment a is 4, b is 20, x is 5, y is 10 and z is 20.

In a preferred embodiment a is 10, b is 150, x is 10, y is 15, and z is 10.

In a preferred embodiment a is 10, b is 200, x is 20, y is 5, and z is 20.

In a preferred embodiment a is 15, b is 10, x is 0, y is 10, and z is 20.

In a preferred embodiment a is 20, b is 1, x is 10, y is 10, and z is 10.

EXAMPLES

The compounds of the present invention are made from commercially available raw materials.

Raw Materials

COLD PRESSED RASPBERRY SEED OIL

Cold Presses Raspberry seed oil is an item of commerce sold by Regal Trade & Consult LLC. of Hoboken, N.J. It is processed using U.S. Pat. No. 6,391,345 issued May 2002, only applied to raspberry seed oil not cranberry seed oil.

DIMETHICONE COPOLYOLS

The raw material silicone compounds of the current invention are commercially available from Siltech LLC, Dacula Ga.

| Example | a | b | x | y | z |
|---|---|---|---|---|---|
| 1 | 1 | 0 | 0 | 0 | 5 |
| 2 | 4 | 0 | 0 | 0 | 5 |
| 3 | 4 | 8 | 5 | 4 | 5 |
| 4 | 4 | 10 | 20 | 20 | 20 |
| 5 | 4 | 100 | 20 | 0 | 20 |
| 6 | 4 | 20 | 5 | 0 | 20 |
| 7 | 10 | 150 | 10 | 15 | 10 |
| 8 | 10 | 200 | 20 | 5 | 20 |
| 9 | 15 | 10 | 0 | 10 | 20 |
| 10 | 20 | 1 | 10 | 10 | 10 |

General Procedure

To grams of 400 grams of Cold Pressed Raspberry seed oil is added the specified amount of the specified dimethicone copolyol (examples 1–10). Next 0.1% of a suitable esterification catalyst is added. The catalyst is selected from the group consisting of methane sulfonic acid, tin compounds and titinate compounds. The preferred catalyst is dilauryl tin oxide.

The reaction mass is heated to 180–200 C, under good agitation. As the reaction mass is held at temperature, the material clears and becomes homogeneous. The reaction mass is held for eight hours at reaction temperature, then cooled to ambient. The product is used without additional purification.

| Example | Dimethicone Example | Copolyol Grams |
|---|---|---|
| 11 | 1 | 458.0 |
| 12 | 2 | 712.0 |
| 13 | 3 | 1200.0 |
| 14 | 4 | 580.0 |
| 15 | 5 | 1000.0 |
| 16 | 6 | 1200.0 |
| 17 | 7 | 350.0 |
| 18 | 8 | 1205.0 |
| 19 | 9 | 1500.0 |
| 20 | 10 | 1470.0 |

The products are used without any additional purification.

Applications Examples

The compounds of the present invention are water-soluble compounds that have an extraordinary skin feel and provide antioxidant, and other desirable properties from the components that are not removed from the raspberry oil when it is cold processed. The cold processing leaves behind the desirable components, which in turn are not destroyed by the reaction and surprisingly, become water-soluble and delivered to the skin.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A composition, which is prepared by the reaction esterification reaction of:

(a) cold pressed raspberry seed oil and (b) a dimethicone copolyol conforming to the following structure

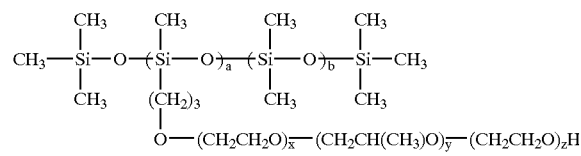

wherein a is an integer ranging from 1 to 20;

b is an integer ranging from 0 to 200; and x, y and z are independently integers ranging from 0 to 20, with the proviso that x+y+z is greater than 5.

2. A composition of claim 1 wherein said esterification is conducted at temperature of between 180 and 220° C.

3. A composition of claim 2 wherein said esterification reaction is conducted using a tin catalyst.

4. A composition of claim 1 wherein a is 4, b is 0, x is 0, y is 0 and z is 5.

5. A composition of claim 1 wherein a is 4, b is 8, x is 5, y is 4, and z is 5.

6. A composition of claim 1 wherein a is 4, b is 10, x is 20, y is 20, and z is 20.

7. A composition of claim 1 wherein a is 4, b is 100, x is 20, y is 0, and z is 20.

8. A composition of claim 1 wherein a is 4, b is 20, x is 5, y is 10 and z is 20.

9. A composition of claim 1 wherein a is 10, b is 150, x is 10, y is 15, and z is 10.

10. A composition of claim 1 wherein a is 10, b is 200, x is 20, y is 5, and z is 20.

11. A composition of claim 1 wherein a is 15, b is 10, x is 0, y is 10, and z is 20.

12. A composition of claim 1 wherein a is 20, b is 1, x is 10, y is 10, and z is 10.

13. A composition of claim 2 wherein a is 4, b is 0, x is 0, y is 0 and z is 5.

14. A composition of claim 2 wherein a is 4, b is 8, x is 5, y is 4, and z is 5.

15. A composition of claim 2 wherein a is 4, b is 10, x is 20, y is 20, and z is 20.

16. A composition of claim 2 wherein a is 4, b is 100, x is 20, y is 0, and z is 20.

17. A composition of claim 2 wherein a is 4, b is 20, x is 5, y is 10 and z is 20.

18. A composition of claim 2 wherein a is 10, b is 150, x is 10, y is 15, and z is 10.

19. A composition of claim 2 wherein a is 10, b is 200, x is 20, y is 5, and z is 20.

20. A composition of claim 2 wherein a is 15, b is 10, x is 0, y is 10, and z is 20.

* * * * *